United States Patent
Fischell et al.

[11] Patent Number: 5,938,689
[45] Date of Patent: Aug. 17, 1999

[54] ELECTRODE CONFIGURATION FOR A BRAIN NEUROPACEMAKER

[75] Inventors: Robert E. Fischell, Dayton, Md.; David R. Fischell, Fair Haven, N.J.

[73] Assignee: NeuroPace, Inc., Fair Haven, N.J.

[21] Appl. No.: 09/070,974

[22] Filed: May 1, 1998

[51] Int. Cl.[6] .................................................. A61N 1/36
[52] U.S. Cl. .............................. 607/45; 607/2; 607/116; 607/148; 600/378; 600/544
[58] Field of Search .................................. 607/2, 45, 46, 607/62, 116, 139, 148, 149, 152; 600/372, 373, 376, 377, 378, 393, 644

[56] References Cited

U.S. PATENT DOCUMENTS

| | | | |
|---|---|---|---|
| 3,850,161 | 11/1974 | Liss | 607/45 |
| 3,918,461 | 11/1975 | Cooper | 607/45 |
| 4,308,873 | 1/1982 | Maynard | 600/378 |
| 4,702,254 | 10/1987 | Zabara | 128/421 |
| 4,850,359 | 7/1989 | Putz | 607/116 |
| 4,903,702 | 2/1990 | Putz | 600/378 |
| 5,299,569 | 4/1994 | Wernicke et al. | 607/405 |
| 5,411,540 | 5/1995 | Edell et al. | 607/116 |
| 5,752,979 | 5/1998 | Benabid | 607/45 |

Primary Examiner—William E. Kamm
Assistant Examiner—Kennedy J. Schaetzle

[57] ABSTRACT

Disclosed herein are several unique configurations of electrodes for stimulation of brain tissue. Specifically, a configuration of electrodes is disclosed that has at least one electrode on the brain's surface and at least one additional electrode located deep within the tissue of the brain. It is envisioned that all such electrodes would be located in close proximity to a particular region of the brain such as an epileptic focus. It is further envisioned that several brain surface electrodes would be used in conjunction with several deep brain electrodes. Specifically, it is envisioned that all surface electrodes would be electrically joined together and all deep electrodes would be electrically joined together. In this way, when a source of electrical current is connected to those electrodes, a particular region of the brain could be surrounded by a "curtain" of electrical current that can be used to depolarize neurons at the perimeter of the region so as to prevent any electrical signal originating in that region from being transmitted beyond that region to the rest of the brain. Sub-surface electrodes placed between 1 and 10 mm below the brain's surface could also be used with either brain surface electrodes or deep brain electrodes.

13 Claims, 4 Drawing Sheets

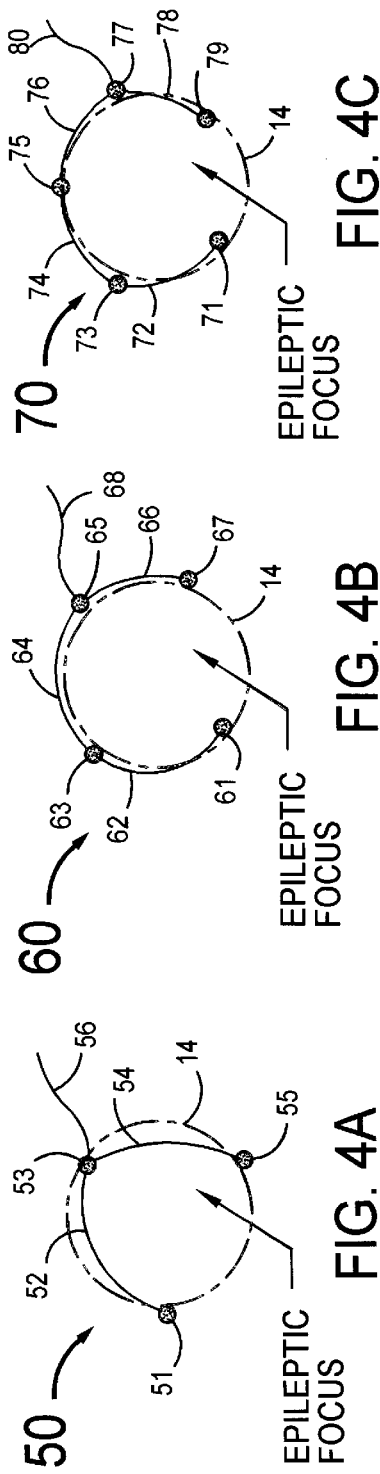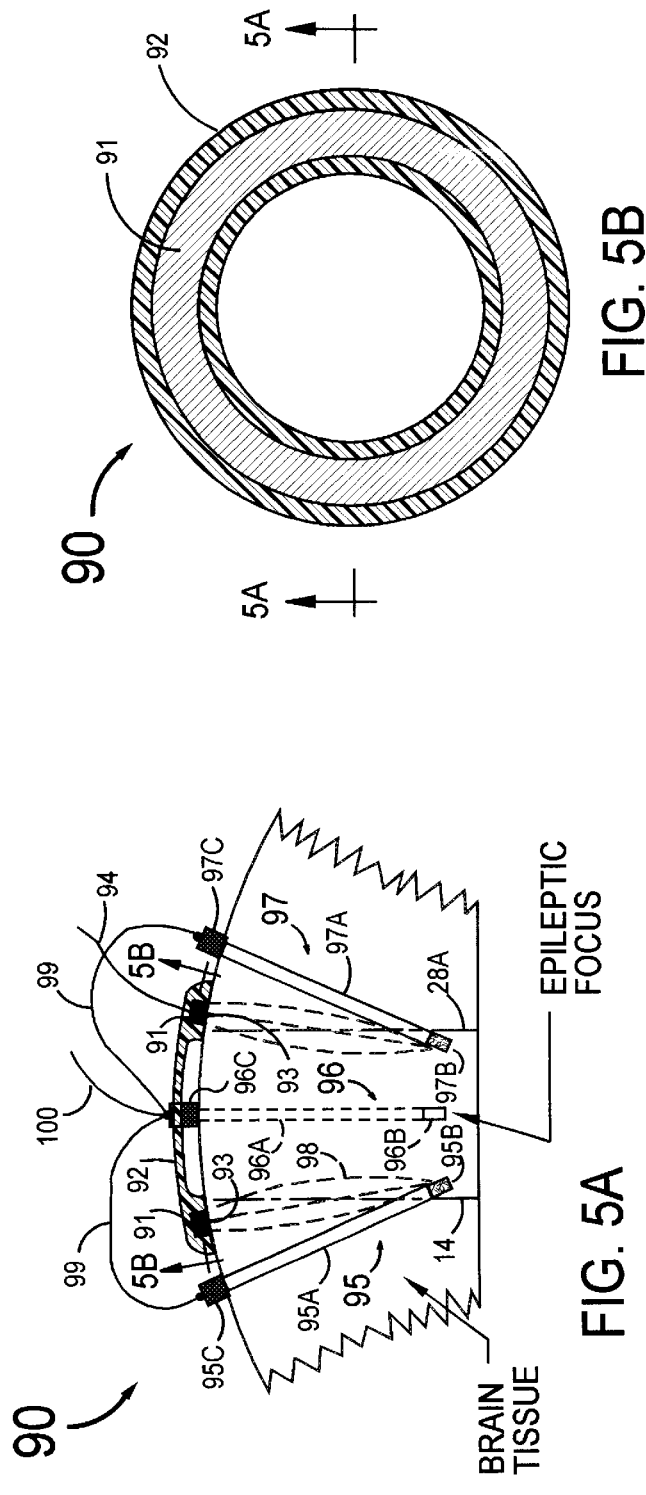

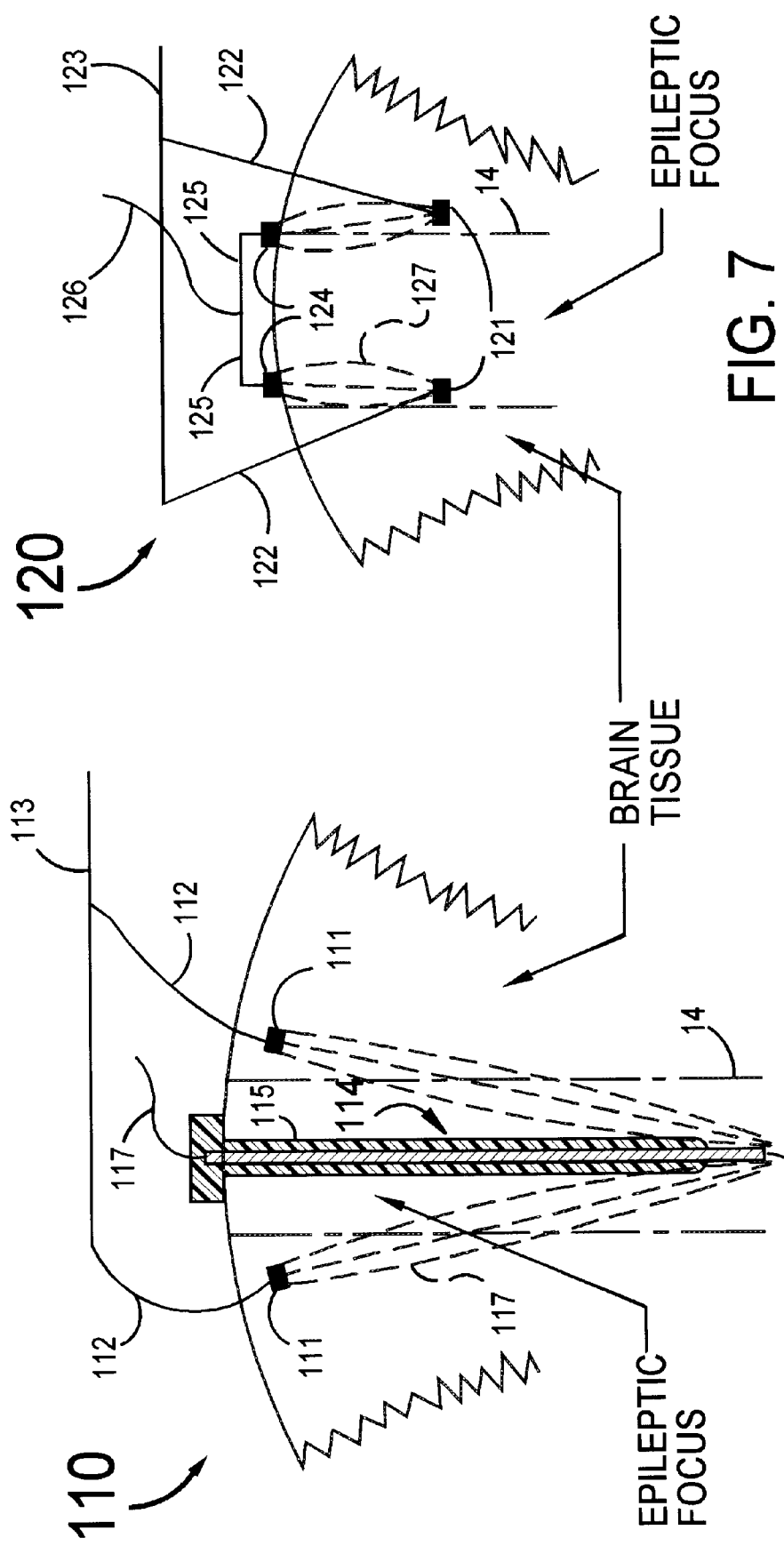

ELECTRODE CONFIGURATION FOR A BRAIN NEUROPACEMAKER

FIELD OF USE

This invention is in the field of devices to treat neurological diseases that originate in the brain.

BACKGROUND OF THE INVENTION

There are several neurological diseases that are characterized by certain electrical discharges that can permeate throughout the brain causing certain human dysfunctions such as an epileptic seizure or a migraine headache.

In U.S. patent application Ser. No. 08/957,869 by Fischell et al (which is included herein by reference) there is described an implantable system that uses electrical stimulation for the treatment of neurological diseases such as epilepsy or migraine headache. However, the Fischell et al application does not describe in detail the configuration of electrodes that are best suited for stimulation of brain tissue.

In U.S. Pat. No. 4,844,075 by Liss, et al, several brain electrodes are described, but Liss does not envision any combination of brain surface electrodes with deep brain electrodes for optimizing the flow path for electrical currents for the treatment of neurological diseases.

SUMMARY OF THE INVENTION

The present invention is a unique configuration of electrodes for stimulation of brain tissue. Specifically, a configuration of electrodes is disclosed that has at least one electrode on the brain's surface and at least one additional electrode located deep within the tissue of the brain. It is envisioned that all such electrodes would be located in close proximity to a particular region of the brain such as an epileptic focus.

It is further envisioned that several brain surface electrodes would be used in conjunction with several deep brain electrodes. Specifically, it is envisioned that all surface electrodes would be electrically joined together and all deep electrodes would be electrically joined together. In this way, a particular region of the brain could be surrounded by a "curtain" of electrical current that can be used to depolarize neurons at the perimeter of the region so as to prevent any electrical signal originating in that region from being transmitted beyond that region to the rest of the brain. Thus an aberrant electrical signal originating in, for example, an epileptic focus would not be transmitted to the rest of the brain thus preventing the clinical manifestations of an epileptic seizure from occurring.

Thus it is an object of this invention to have at least one brain surface electrode and at least one deep brain electrode that cooperate to provide an electrical current between the two so as to depolarize the brain tissue that lies between the at least two electrodes.

Another object of this invention is to have a multiplicity of brain surface electrodes and a multiplicity of deep brain electrodes so as to create a "curtain" of electrical current in between so as to depolarize the brain neurons that lie between the two sets of electrodes.

Still another object of this invention is to use brain electrodes at various depths beneath the surface of the brain to treat a specific neurological disorder.

These and other objects and advantages of this invention will become obvious to a person of ordinary skill in this art upon reading of the detailed description of this invention including the associated drawings.

BRIEF DESCRIPTION OF THE DRAWINGS

FIG. 4A is a top view of the brain's surface showing an array of exactly three brain surface electrodes each placed in the vicinity of the boundary of an epileptic focus.

FIG. 4B is a top view of the brain's surface showing an array of exactly four brain surface electrodes each placed in the vicinity of the boundary of an epileptic focus.

FIG. 4C is a top view of the brain's surface showing an array of exactly five brain surface electrodes each placed in the vicinity of the boundary of an epileptic focus.

FIG. 5A is a cross section of a human brain showing the cross section of a toroidally shaped ring electrode having an annular bottom surface of the electrode placed in contact with the brain's surface in the vicinity of the boundary of an epileptic focus and also showing a multiplicity of deep electrodes electrically connected together. All other surfaces of the rings electrode are covered with electrical insulation.

FIG. 5B is a cross section of the ring electrode and the deep electrodes at section 5B–5B of FIG. 5A.

FIG. 6 is a cross section of a human brain showing an array of sub-surface electrodes electrically connected together being used with a single deep electrode to provide a sheet of electrical current in the vicinity of the boundary of the epileptic focus.

FIG. 7 is a cross section of a human brain showing an array of brain surface electrodes that are electrically connected together being used with an array of sub-surface electrodes that are electrically connected together to form a sheet of electrical current in the vicinity of the boundary of the epileptic focus.

DETAILED DESCRIPTION OF THE DRAWINGS

Figure 1:
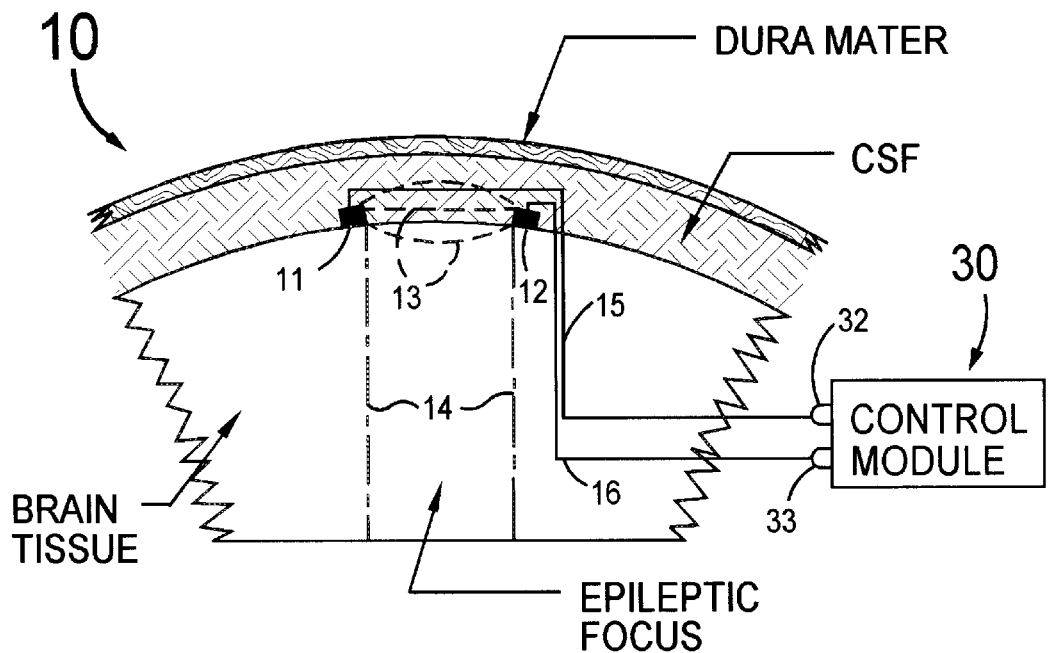
FIG. 1 is a cross section through brain tissue showing a pair of brain surface electrodes with electrical currents therebetween.

FIG. 1 is a cross section of brain tissue at the site of an epileptic focus in the brain of a human subject. The epileptic focus is that region of the brain of an epileptic patient which is believed to be the source of that patient's epileptic seizures. In FIG. 1 we see that the phantom lines indicate the location of the boundary 14 of the epileptic focus within the brain tissue. FIG. 1 also shows an electrode configuration 10 consisting of a pair of brain surface electrodes 11 and 12 that are connected by the wires 15 and 16 to the terminals 32 and 33 respectively of a control module 30. The electric current field lines 13 between two such brain electrodes 11 and 12 are also shown in FIG. 1. Although electrical stimulation between the electrodes 11 and 12 could have some effect on the neurons within the epileptic focus, the electric current density in the tissue of the epileptic focus would frequently be too low to produce the desired effect of aborting an epileptic seizure.

Figure 2:
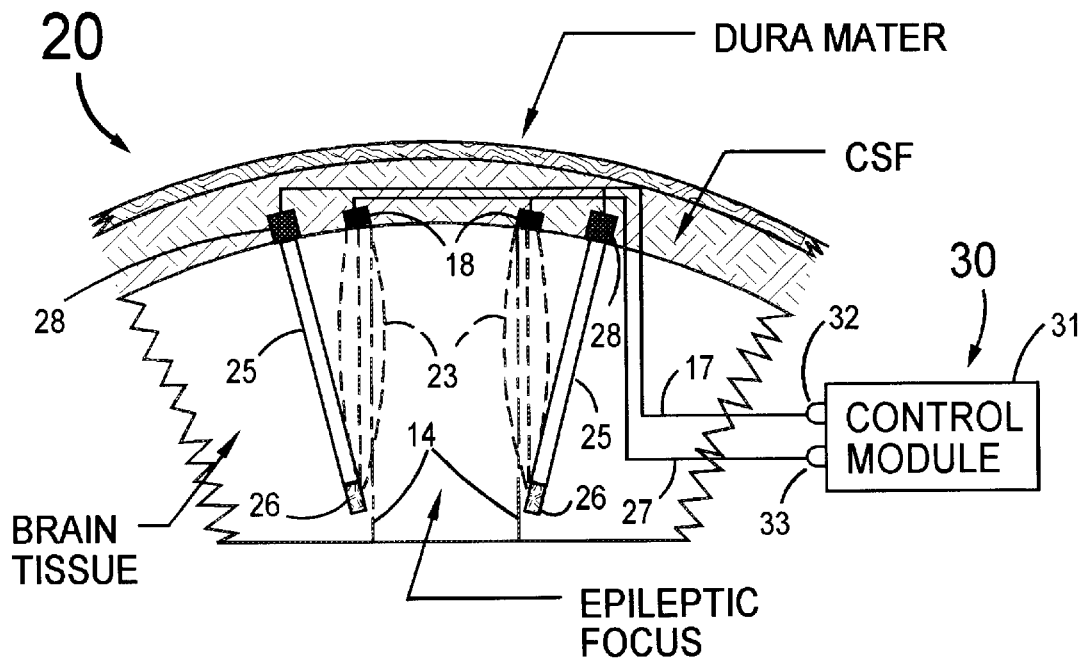
FIG. 2 is a cross section through the brain tissue showing a set of brain surface electrodes and a set of deep brain electrodes and a curtain of electrical current between the two sets of electrodes.

FIG. 2 is a cross section of brain tissue at the site of an epileptic focus having an outer boundary 14 and an electrodes configuration 20. In addition to the brain surface electrodes 18, the configuration 20 includes a set of deep electrodes 26 having an insulated shaft portion 25 and an electrical connector 28 placed at the proximal end of the insulated shaft portion 25. "Deep" electrodes are defined as those electrodes placed deeper than 10 mm below the surface of the brain.

FIG. 2 also shows the control module 30 having a metal case 31 that contains electrical circuitry for detecting an epileptic seizure before presentation of the clinical manifestations of that seizure. The electronics module 30 includes electrical and electronic circuitry to stimulate the brain to abort an epileptic seizure before the onset of clinical manifestations. The control module 30 would also contain circuitry to record multiple channels of EEG data. The module 30 would have at least two sets of electrical terminals 32 and 33, with (typically) one of the terminals being at ground potential. It is also envisioned that each of the terminals 32 and 33 could have a non-grounded electrical signal with the case 31 of the electronics module 30 being maintained at ground potential.

The wire 27 connects the terminal 33 to the brain surface electrodes 18. The wire 17 connects the output terminal 32 to the deep electrodes 26. This connection would be made at the top of the insulated shaft 25 by an electrical connector 28 that electrically and mechanically joins the wire 17 to the deep electrodes 26.

When there is a voltage between the two terminal 32 and 33 and all the brain surface electrodes 18 are connected to the output terminal 33 and all the deep electrodes 26 are connected to the output terminal 32, there will be a sheet of electrical current 23 created at or near the boundary 14 of the epileptic focus. If the electric current density in the brain tissue in the vicinity of the boundary 14 is high enough as a result of the electric current sheet 23, then the brain neurons that experience such a current density would be depolarized. In a depolarized state, the neurons at the epileptic focus boundary 14 would become incapable of spreading an aberrant electrical signal that would result in the clinical manifestations of an epileptic seizure. Therefore, the electrode configuration shown in FIG. 2 can be used to prevent the clinical manifestations of an epileptic seizure when the electric field lines causing an appropriate current density in the brain tissue are generated by means of an output electrical current signal from the control module 30.

Figure 3:
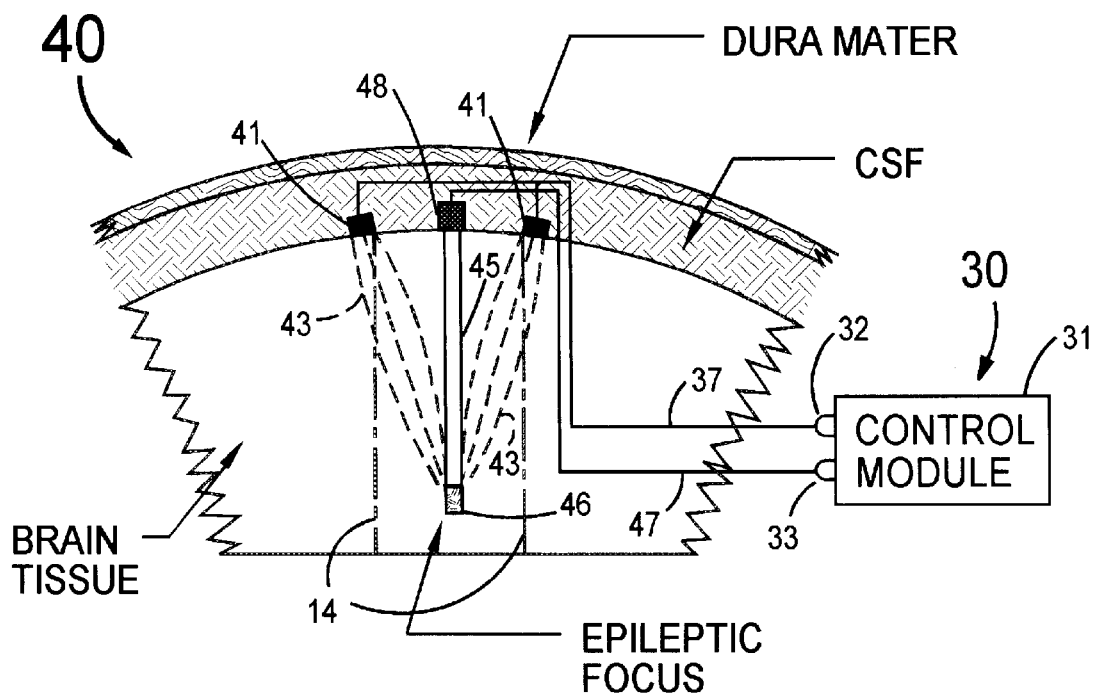
FIG. 3 is a cross section through the brain tissue showing a set of brain surface electrodes and a single deep brain electrode and a curtain of electrical current between the two sets of electrodes.

FIG. 3 is a cross section of brain tissue into which is placed an electrode configuration 40 consisting of brain surface electrodes 41 and a single deep electrode 46. The deep electrode 46 is electrically connected by the wire 47 to the terminal 33 of the control module 30 by means of an electrical connector 48 that is situated at the proximal end of the insulated shaft 45. The surface electrodes 41 are electrically connected to the terminal 32 of the control module 30 by means of the wire 37. An output electrical current generated in the control module 30 generates the electric field lines 43 as shown in FIG. 3. If the electric current density in the brain tissue which results from the generation of these field lines 43 is strong enough to cause depolarization of enough neurons in the vicinity of the epileptic focus, then an epileptic seizure can be prevented.

Although only three different configurations of brain electrodes have been illustrated in FIGS. 1,2 and 3, it is readily envisioned to utilize a large variety of electrode configurations. Specifically, one could have one or more brain surface electrodes operating with one or more deep electrodes. Also envisioned is having some electric field lines generated between a certain subset of surface electrodes and/or between certain deep electrodes. Furthermore, one could use deep electrodes at a variety of depths below the brain's surface with or without brain surface electrodes. Some particularly valuable electrode configurations would include sub-surface electrodes placed between 1 and 10 mm beneath the brain's surface. One or more of such brain sub-surface electrodes could be used with one or more brain surface electrodes or one or more deep brain electrodes. It is further envisioned that one set of electrodes could be used for detection of an epileptic seizure, and a different set of electrodes could be used for electrical stimulation to abort a seizure. Still further it is envisioned that the case 31 of the control module 30 could act as one electrode with the other electrode being a single deep electrode or a single sub-surface electrode.

FIGS. 4A, 4B, 4C, 5A, 5B, 6 and 7 illustrate several different types of electrode configurations all of which (except for FIG. 7) are utilized with deep electrodes. FIG. 4A is a top view of the brain surface showing a surface electrode array 50 having exactly three surface electrodes 51, 53 and 55 that are electrically connected together by interconnecting wires 52 and 54 with the wire 56 electrically connecting all the electrodes 51, 53 and 55 to one terminal of the control module 30 (as shown in FIG. 2). FIG. 4B is a top view of the brain surface showing a surface electrode array 60 having exactly four electrodes 61, 63, 65 and 67 that are electrically connected together by the wires 62, 64 and 66 with the wire 68 electrically connecting all the electrodes 61, 63, 65 and 67 to the control module 30. FIG. 4C is a top view of the brain surface showing a surface array 70 having exactly five electrodes 71, 73, 75, 77 and 79 that are electrically connected by the interconnecting wires 72, 74, 76 and 78 with the wire 80 electrically connecting all the electrodes 71, 73, 75, 77 and 79 to the control module 30. As shown in FIGS. 4A, 4B and 4C each electrode could be within or outside the boundary 14 of an epileptic focus, or the electrode could be placed exactly on the boundary 14. Most importantly, all the surface electrodes are in the vicinity of the boundary 14 of the epileptic focus. This structural arrangement of the electrodes is required in order to produce a sheet of electrical current between any array of brain surface electrodes and one or more deep brain electrodes; the sheet of electrical current being situated in the vicinity of the boundary 14 of an epileptic focus for example as seen in FIG. 2.

It is further conceived that some or all of the electrodes in any configuration could be used to sense a precursor signal that occurs in most patients prior to the onset of the clinical manifestations of an epileptic seizure. Such a signal is particularly detectable with electrodes that are located in close proximity to an epileptic focus. Thus it would be practical with electrode configurations that utilize at least one brain surface electrode and/or at least one deep brain electrode to both sense a precursor of an epileptic seizure and to generate a responsive electrical signal that can abort such a seizure. Furthermore, the sub-surface or deep electrode could each be bipolar or multi-polar electrodes as is well known in the art of brain electrodes.

A valuable electrode configuration could consist of a single ring type of brain surface electrode that is used with one or more deep brain electrodes or one or more sub-surface electrodes. The ring type of surface electrode would typically have a diameter between 1 and 3 centimeters and would be insulated on its outer surface but would be electrically conducting in the form of an annular surface where it makes contact with the brain's surface. Such a design would be simpler to use as compared to a multiplicity of individual brain surface electrodes which are electrically joined together by means of wires.

FIGS. 5A and 5B illustrate an electrode configuration 90 consisting of a ring electrode 91 in conjunction with deep brain electrodes 95, 96 and 97. The ring electrode 91 is a toroidally shaped metal conductor 91 having an annular electrically conducting bottom surface 93 that is placed directly on the brain's surface. The ring electrode 91 is electrically connected by a wire 94 to a first terminal of the control module 30. The insulating disc 92 covers some or all of the surfaces of the ring electrode 91 except for the annular surface 93 that is in contact with the surface of the brain. The deep electrodes 95, 96 and 97 have insulated coverings 95A, 96A and 97A, distal end electrodes 95B. 96B and 97B and proximal end electric terminals 95C, 96C and 97C. All the deep electrodes 95, 96 and 97 are electrically connected together by the wires 99 which connect to the wire 100 thereby connecting all the distal end electrode terminals 95C, 96C and 97C to a second terminal of the control module 30 (of FIG. 2). Most importantly, FIG. 5A illustrates the basic inventive concept of this invention which is that electrodes are positioned to create a sheet of electrical current 98 in the vicinity of the boundary 14 of the epileptic focus when the control module 30 generates a responsive electrical stimulation signal. It is this sheet of electrical current that, if sufficiently strong, can depolarize the neurons located in the vicinity of the boundary 14 thus preventing the spread of any aberrant electrical signal from the epileptic focus to the remainder of the brain thereby preventing the clinical manifestations of an epileptic seizure.

FIG. 6 is a cross section of brain tissue showing an electrode array 110 consisting of sub-surface electrodes 111 that are connected by the wires 112 to the wire 113 that connects to a first terminal of the control module 30 as shown in FIG. 2 and a single deep electrode 114 having an electrically conducting distal end electrode 116 and an insulating covering 115. The proximal end of the deep electrode 114 is connected by the electrical wire 117 to a second terminal of the control module 30. Although exactly two sub-surface electrodes are shown in FIG. 6, it should be understood that one, three, four or five sub-surface electrodes could be used. Most importantly, FIG. 6 shows the electrical current sheet 117 in the vicinity of the boundary 14 of the epileptic focus within the brain tissue. It is this current sheet that, when properly applied by means of the control module 30, can prevent an epileptic seizure.

FIG. 7 is a cross section of brain tissue showing an electrode configuration 120 consisting of surface electrodes 124 joined by the wires 125 to the wire 126 that is connected to a first terminal of the control module 30. FIG. 7 also shows sub-surface electrodes 121 connected by the wires 122 to the wire 123 that connects to a second terminal of the control module 30. Between the surface electrodes 124 and the subsurface electrodes 121 an electrical current sheet 127 can be created in the vicinity of the boundary 14 of the epileptic focus. It is expected that the electrode configuration 120 will be less effective in stopping an epileptic seizure as compared to other configurations that can surround more of the boundary 14 of the epileptic focus.

It should be understood that the surface electrodes shown in FIGS. 1, 2, 3, 4A, 4B, 4C, 5A, 5B and 7 can be used with one or more deep electrodes in a configuration as generally illustrated in FIG. 2. In all cases, what is important is that a sheet of electrical current is created between a configuration of surface (or sub-surface) electrodes and one or more deep electrodes with all the surface (or sub-surface) electrodes electrically connected together and all the deep electrodes electrically connected together. Thus neurons in the vicinity of the boundary 14 of the epileptic focus (as seen in FIGS. 2, 3, 4A, 4B, 4C, 5A, 6 and 7) will experience a depolarizing electrical current density that can prevent the clinical manifestations of an epileptic seizure. The "vicinity of the boundary of the epileptic focus" is defined herein as that which is generally shown in FIGS. 2, 3, 4A, 4B, 4C, 5A, 6 and 7 as the position of the sheet of electrical current relative to the boundary 14 of the epileptic focus.

Various other modifications, adaptations, and alternative designs are of course possible in light of the above teachings. Therefore, it should be understood at this time that within the scope of the appended claims the invention may be practiced otherwise than as specifically described herein.

What is claimed is:

1. A system for the electrical stimulation of brain tissue, the system comprising:
    at least one brain surface electrode;
    at least one deep brain electrode; and
    a control module adapted to provide a stimulation electrical current between the at least one brain surface electrode and the at least one deep brain electrode, the control module having a first terminal and a second terminal, the control module's first terminal being electrically coupled to the at least one brain surface electrode and the control module's second terminal being electrically coupled to the at least one deep brain electrode, the at least one brain surface electrode and the at least one deep brain electrode being placed in a configuration within the brain tissue so that the stimulation electrical current forms a sheet of electrical current that is applied in the vicinity of the boundary of an epileptic focus that is located within the brain tissue thus depolarizing brain neurons located in the vicinity of the epileptic focus.

2. The system of claim 1 wherein there is exactly one deep brain electrode.

3. The system of claim 2 wherein there are exactly two brain surface electrodes.

4. The system of claim 2 wherein there are exactly three brain surface electrodes.

5. The system of claim 2 wherein there are exactly four brain surface electrodes.

6. The system of claim 2 wherein there are exactly five brain surface electrodes.

7. The system of claim 2 wherein the at least one brain surface electrode is exactly one electrode and is in the form of a ring that has an annular bottom surface that is electrically conducting and makes contact with the surface of the brain.

8. The system of claim 1 wherein the at least one brain surface electrode is one electrode in the form of a ring having an annular bottom surface in the form of an annulus that makes electrical contact with the surface of the brain, the ring being adapted to cooperate with the at least one deep brain electrode to create the sheet of electrical current in the vicinity of the boundary of the epileptic focus.

9. The system of claim 8 wherein the ring has a diameter between 1 and 3 centimeters.

10. The system of claim 8 wherein the ring is electrically insulated on each of its surfaces except for the ring's annular bottom surface that is in contact with the brain, the annular bottom surface being electrically conducting.

11. A system of brain electrodes for the electrical stimulation of brain tissue, the system comprising:
    at least one brain sub-surface electrode;
    at least one deep brain electrode; and
    a control module adapted to provide a stimulation electrical current between the at least one brain sub-surface electrode and the at least one deep brain electrode, the control module having a first terminal and a second terminal, the control module's first terminal being electrically coupled to the at least one brain sub-surface electrode and the control module's second terminal being electrically coupled to the at least one deep brain electrode, the at least one brain sub-surface electrode and the at least one deep brain electrode being placed in a configuration within the brain tissue so that the stimulation electrical current forms a sheet of electrical current that is applied in the vicinity of the boundary of an epileptic focus that is located within the brain tissue thus depolarizing brain neurons located in the vicinity of the epileptic focus.

12. A system of brain electrodes for the electrical stimulation of brain tissue, the system comprising:

at least one brain sub-surface electrode;

at least one brain surface electrode; and a control module adapted to provide a stimulation electrical current between the at least one brain surface electrode and at least one sub-surface electrode, the control module having a first terminal and a second terminal, the control module's first terminal being electrically coupled to the at least one brain sub-surface electrode and the control module's second terminal being electrically coupled to the at least one surface electrode, the at least one brain surface electrode and the at least one brain sub-surface electrode being placed in a configuration within the brain tissue so that the stimulation electrical current forms a sheet of electrical current that is applied in the vicinity of the boundary of an epileptic focus that is located within the brain tissue thus depolarizing brain neurons located in the vicinity of the epileptic focus.

13. A method for establishing a sheet of electrical current in the vicinity of the boundary of an epileptic focus in the brain tissue of a human subject, the method comprising the following steps:

(a) placing within the body of the human subject a control module that has a first electrical terminal and a second electrical terminal, the control module being capable of providing an electrical current across one or more configurations of electrodes which electrode configurations are placed within the body of a human subject;

(b) placing a configuration of one or more surface electrodes onto the surface of the brain of the human subject in the vicinity of the boundary of an epileptic focus each of the one or more surface electrodes being electrically connected to the first terminal of the control module;

(c) placing a configuration of one or more deep brain electrodes at a depth of greater than 1 cm into the brain tissue in the vicinity of the boundary of an epileptic focus with each of the deep brain electrodes being electrically connected to the second terminal of the control module; and (d) actuating the control module so as to create a sheet of electrical current between the configurations of the one or more surface electrodes and the one or more deep brain electrodes thus placing the sheet of electrical current in the vicinity of the boundary of the epileptic focus so as to depolarize neurons in the vicinity of the boundary of the epileptic focus.

* * * * *